United States Patent [19]

Enomoto et al.

[11] Patent Number: 5,234,938
[45] Date of Patent: Aug. 10, 1993

[54] BENZIMIDAZOLE DERIVATIVE, ITS INTERMEDIATE COMPOUNDS AND AN AGRICULTURAL AND HORTICULTURAL FUNGICIDE CONTAINING THE BENZIMIDAZOLE DERIVATIVE AS AN ACTIVE INGREDIENT

[75] Inventors: Masayuki Enomoto, Takarazuka; Junya Takahashi, Hyogo; Tomoyuki Kusaba, Toyonaka; Masayo Sugano, Osaka; Rei Matsunaga, Takarazuka; Masahiro Tamaki, Toyonaka, all of Japan

[73] Assignee: Sumitomo Chemical Company, Limited, Osaka, Japan

[21] Appl. No.: 792,477

[22] Filed: Nov. 15, 1991

[30] Foreign Application Priority Data

Nov. 20, 1990 [JP] Japan ................... 2-316723

[51] Int. Cl.⁵ .................. A01N 43/52; C07D 235/30; C07D 235/24
[52] U.S. Cl. ................... 514/395; 514/394; 548/309.7; 548/310.1; 548/310.4
[58] Field of Search .................. 548/329, 331, 309.7, 548/310.1, 310.4; 514/394, 395

[56] References Cited

U.S. PATENT DOCUMENTS

| | | | |
|---|---|---|---|
| 3,501,492 | 3/1970 | Floyd | 548/332 |
| 3,576,818 | 4/1971 | Samuel et al. | 548/331 |
| 4,536,502 | 8/1985 | Giraudon et al. | 514/227 |
| 4,767,444 | 8/1988 | Heywang et al. | 71/92 |

FOREIGN PATENT DOCUMENTS

| | | |
|---|---|---|
| 0219192 | 4/1987 | European Pat. Off. . |
| 0251012 | 1/1988 | European Pat. Off. . |
| 0251013 | 1/1988 | European Pat. Off. . |
| 0251014 | 1/1988 | European Pat. Off. . |
| 2601010 | 1/1988 | France . |
| 60-181053 | 9/1985 | Japan . |
| 61-103873 | 5/1986 | Japan . |
| 62-205063 | 9/1987 | Japan . |
| 62-240666 | 10/1987 | Japan . |
| 63-211270 | 9/1988 | Japan . |
| 2163154 | 2/1986 | United Kingdom . |

Primary Examiner—Patricia L. Morris
Attorney, Agent, or Firm—Stevens, Davis, Miller & Mosher

[57] ABSTRACT

A benzimidazole derivative having the formula,

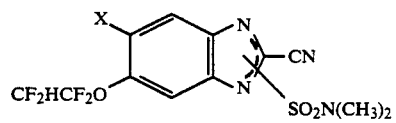

wherein X is halogen, is produced by reacting a compound having the formula,

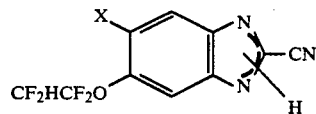

wherein X is halogen, with dimethylsulfamoyl chloride.

The benzimidazole derivative can be used as an active ingredient in agricultural and horticultural fungicides.

14 Claims, No Drawings

BENZIMIDAZOLE DERIVATIVE, ITS INTERMEDIATE COMPOUNDS AND AN AGRICULTURAL AND HORTICULTURAL FUNGICIDE CONTAINING THE BENZIMIDAZOLE DERIVATIVE AS AN ACTIVE INGREDIENT

The present invention relates to a benzimidazole derivative, a method for producing it, its intermediate compounds and an agricultural and horticultural fungicide containing the benzimidazole derivative as an active ingredient.

Captan, captafol and dithiocarbamate pesticides are known among the widely used agricultural and horticultural fungicides, particularly those used in the fields of late blight and downy mildew. These pesticides, however, do not show a curative effect although they show a preventive effect. Thus, they are unsuitable for control of diseases after attack.

In view of the practice of the application of the pesticides for controlling plant diseases, there is a case wherein the pesticides are applied after slight attack. Consequently, to the pesticides for controlling Phycomycetes which show a particularly rapid advance of disease symptoms, a high preventive efficacy as well as excellent systemic activity and curative efficacy are strongly required. Under the circumstances like this, metalaxyl, N-(2,6-dimethylphenyl)-N-(methoxyacetyl)-DL-alanine methyl ester, excellent in the systemic activity and having a curative activity was developed. However, resistant pathogens appeared in a short time, so that the excellent curative activity of metalaxyl is not sufficiently displayed.

At present, particularly in the field of the control of diseases of grape, appearance of curative agents having a novel function and excellent systemic activity are being desired.

JP-A-58-148864 and JP-A-62-205063 disclose the use of certain kind of benzimidazole derivatives as an active ingredient for fungicides.

These compounds, however, may not always be said to be satisfactory for the reasons that they are insufficient in efficacy to control plant diseases, particularly in terms of efficacy and systemic activity for controlling plant diseases caused by Phycomycetes such as downy mildew, late blight and the like, and also that they give phytotoxicity to plants to be protected.

In view of such situation, the present inventors have extensively studied to develop a compound having excellent efficacy against plant diseases and also giving little phytotoxicity. As a result they have found that the benzimidazole derivative of the present invention has excellent preventive and curative efficacy against plant diseases, is excellent in the systemic activity and further gives no such phytotoxicity as would become a problem to plants to be protected. The present inventors thus attained to the present invention.

According to the present invention, there are provided a benzimidazole derivative (hereinafter referred to as present compound) having the formula (I),

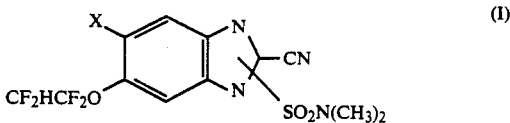

wherein X is halogen; a process for producing the same; its intermediate compounds; and an agricultural and horticultural fungicide comprising the benzimidazole derivative as an active ingredient.

In the above formula (I), halogen includes fluorine, chlorine and bromine, for example.

A method for producing the present compound will be explained in detail.

The present compound is obtained by reacting a benzimidazole compound (hereinafter referred to as compound (II)) having the formula (II),

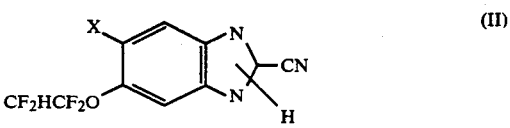

wherein X is as defined above, with dimethylsulfamoyl chloride.

The reaction usually proceeds at a reaction temperature in the range of from room temperature to the refluxing temperature of the solvent and in a reaction time in the range of from a moment to about 24 hours.

The reaction is usually carried out in the presence of a base. Specific examples of the base are tertiary amines (e.g. pyridine, triethylamine, N,N-dimethylaniline, tributylamine, N-methylmorpholine), inorganic bases (e.g. sodium hydroxide, potassium hydroxide, potassium carbonate) and the like.

Referring to the amount of the reagents used for the reaction, the amount of dimethylsulfamoyl chloride is usually 1 to 2 moles per mole of the compound (II), and that of the base is 1 to 7 moles per mole of the compound (II).

In the above reaction, the reaction is usually carried out in the presence of a solvent.

Specific examples of the usable solvent are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate, diethyl carbonate), nitriles (e.g. acetonitrile, isobutyronitrile), amides (e.g. formamide, N,N-dimethylformamide), sulfur compounds (e.g. dimethyl sulfoxide) and the mixtures thereof.

After completion of the reaction, the reaction solution is subjected to usual after-treatments such as extraction with organic solvents, washing with water, concentration of the organic layer under reduced pressure, etc., and then the resulting product is purified if necessary by operations such as chromatography, recrystallization, etc. Thus, the desired present compound can be obtained.

Some examples of the present compounds obtainable by the process explained above are listed below: 2-Cyano-1-dimethylsulfamoyl-5(6)-fluoro-6(5)-(1',1',2',2'-tetrafluoroethoxy)benzimidazole, 5(6)-Chloro-2-cyano-1-dimethylsulfamoyl-6(5)-(1',1',2',2'-tetrafluoroethoxy)- benzimidazole, and 5(6)-Bromo-2-cyano-1-dimethylsulfamoyl-6(5)-(1',1',2'-tetrafluoroethoxy)benzimidazole.

The compound (II) shows tautomerism as follows:

$$\underset{\text{(II-a)}}{\underset{CF_2HCF_2O}{X}\diagdown\underset{H}{\overset{N}{\diagup}}\text{—CN}} \rightleftarrows \underset{\text{(II-b)}}{\underset{CF_2HCF_2O}{X}\diagdown\underset{N}{\overset{N}{\diagup}}\text{—CN}}$$

wherein X is as defined above. Consequently, when the present compound is produced using the compound (II), a compound having the formula (I-a), $$\underset{CF_2HCF_2O}{X}\diagdown\underset{SO_2N(CH_3)_2}{\overset{N}{\diagup}}\text{—CN} \qquad (I\text{-}a)$$

wherein X is as defined above, or the formula (I-b), $$\underset{CF_2HCF_2O}{X}\diagdown\underset{}{\overset{SO_2N(CH_3)_2}{\overset{N}{\diagup}}}\text{—CN} \qquad (I\text{-}b)$$

wherein X is as defined above, or the mixture of (I-a) and (I-b) is obtained depending upon the reaction conditions.

Consequently, the present compound having the formula (I) includes (I-a) and/or (I-b).

The compound (II), which is a starting material for producing the present compound, is obtained by reacting a 2-(trichloromethyl)benzimidazole compound (hereinafter referred to as compound (III)) having the formula (III), $$\underset{CF_2HCF_2O}{X}\diagdown\underset{H}{\overset{N}{\diagup}}\text{—CCl}_3, \qquad (III)$$

wherein X is as defined above, with ammonia.

The reaction usually proceeds at a reaction temperature in the range of from −30° C. to the refluxing temperature of the solvent and in a reaction time in the range of from a moment to about 24 hours.

Referring to the amount of the reagent used for the reaction, the amount of ammonia is usually from 6 moles to a large excess per mole of the compound (III).

In the above reaction, the reaction is usually carried out in the presence of a solvent.

Specific examples of the usable solvent in the reaction are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate, diethyl carbonate), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), water and the mixtures thereof.

After completion of the reaction, the reaction solution is neutralized with an inorganic acid (e.g. hydrochloric acid) and then subjected to after-treatments such as extraction with organic solvents, washing with water, concentration of the organic layer, etc. Thus, the desired compound can be obtained.

The compound (III) can be obtained by reacting an o-phenylenediamine compound having the formula (IV), $$\underset{CF_2HCF_2O}{X}\diagdown\diagup\underset{NH_2}{\overset{NH_2}{}}\qquad (IV)$$

wherein X is as defined above, with a trichloroacetoimidate compound having the formula (V), $$CCl_3C(=NH)OR \qquad (V),$$

wherein R represents a lower (usually $C_1$–$C_6$) alkyl group.

The reaction usually proceeds at a reaction temperature in the range of from −30° C. to the refluxing temperature of the solvent and in a reaction time in the range of from a moment to 24 hours.

Referring to the amount of the reagent used for the reaction, the amount of the trichloroacetoimidate compound (V) is usually about 1 to about 2 moles per mole of the o-phenylenediamine compound (IV).

In the above reaction, the reaction is usually carried out in the presence of a solvent.

Specific examples of the usable solvent in the reaction are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), organic acids (e.g. formic acid, acetic acid, propionic acid), water and the mixtures thereof.

After completion of the reaction, the reaction solution is subjected, for example, to after-treatments such as pouring into ice water and separation of the resulting crystals by filtration, or extraction with organic solvents, washing with water, concentration, etc. The resulting product is then purified if necessary by operations such as chromatography, recrystallization, etc. Thus, the desired compound can be obtained.

The compound (III) can also be obtained by reacting the o-phenylenediamine compound (IV) with trichloroacetyl chloride to obtain a 2-aminotrichloroacetoanilide compound and ring-closing the 2-aminotrichloroacetoanilide compound.

The ring-closure reaction usually proceeds in the temperature range of from 40° C. to the refluxing temperature of the solvent and in the time range of from a moment to 24 hours.

In the above reaction, the reaction is usually carried out in the presence of a solvent.

Specific examples of the usable solvent in the reaction are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate, diethyl carbonate), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), water and the mixtures thereof.

The reaction of the o-phenylenediamine compound (IV) with trichloroacetyl chloride can be carried out in the same manner as in the foregoing reaction of the compound (II) with dimethylsulfamoyl chloride.

The o-phenylenediamine derivative having the formula (IV) is obtained by reducing an o-nitroaniline compound having the formula (VI),

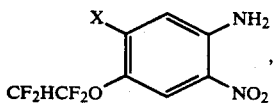  (VI)

wherein X is as defined above.

For reducing the o-nitroaniline compound, a method of carrying out reduction using sodium sulfide or sodium hydrogensulfide in a mixture of water and a lower alcohol such as methanol, ethanol, etc., can be used, for example. The reaction usually proceeds in the temperature range of from 50° C. to the refluxing temperature of the solvent and within 12 hours.

Also, the reduction can be carried out by a method using iron powders, zinc powders or tin powders in a mixture of water and either an organic acid (e.g. acetic acid) or an inorganic acid (e.g. hydrochloric acid, sulfuric acid). The reaction can be usually carried out in the temperature range of from 30° C. to 100° C., and the reaction can be usually completed within 12 hours.

Also, a reduction method in which hydrogenation is carried out in the temperature range of usually from 0° C. to 60° C. at normal pressure or under pressure using a catalyst (e.g. platinum dioxide, palladium-carbon) in an organic solvent (e.g. ethanol, ethyl acetate) can be used.

The o-nitroaniline compound (VI) is obtained by hydrolyzing an o-nitroanilide compound having the formula (VII),

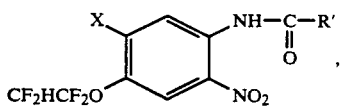  (VII)

wherein X is as defined above, and R' is a lower (usually $C_1$-$C_6$) alkyl group.

The reaction usually proceeds at a reaction temperature in the range of from room temperature to the refluxing temperature of the solvent or 100° C. and in a reaction time in the range of from a moment to about 24 hours.

The above reaction is usually carried out in the presence of a base or acid. Specific examples of the base used are inorganic bases such as sodium hydroxide, potassium hydroxide, etc., and those of the acid are inorganic acids such as hydrochloric acid, sulfuric acid, etc.

Referring to the amount of the reagent used for the reaction, the amount of the base or acid is from a catalytic amount to a large excess per mole of the o-nitroanilide compound (VII).

Use of solvent should be dictated by the kind of the base or acid used, including the case of no solvent used.

When a solvent is used, it includes aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), organic acids (formic acid, acetic acid, propionic acid), water and the mixtures thereof.

The o-nitroanilide compound (VII) is obtained by nitrating an anilide compound having the formula (VIII)

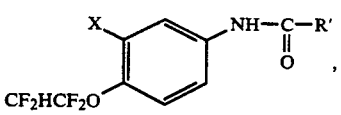  (VIII)

wherein X and R' are as defined above.

The reaction proceeds at a reaction temperature in the range of from −40° C. to 20° C., preferably from −30° C. to +5° C., and in a reaction time in the range of from a moment to about 24 hours.

As the nitrating agent, fuming nitric acid, nitric acid, sodium nitrate and potassium nitrate can be used. As the solvent, acetic acid, acetic anhydride, sulfuric acid, fuming sulfuric acid, water and the mixtures thereof can be used.

The anilide compound (VIII) is obtained by acylating an aniline compound having the formula (IX),

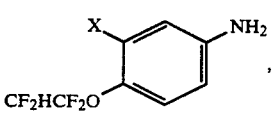  (IX)

wherein X is as defined above.

The reaction usually proceeds at a reaction temperature in the range of from room temperature to the refluxing temperature of the solvent or 120° C. and in a reaction time in the range of from a moment to about 24 hours.

The reaction is usually carried out in the presence of a base or acid. Specific examples of the usable base are tertiary amines (e.g. pyridine, triethylamine, N,N-dimethylaniline, tributylamine, N-methylmorpholine), inorganic bases (e.g. sodium hydroxide, potassium hydroxide, potassium carbonate) and the like. Specific examples of the usable acid are organic acids (e.g. acetic acid, propionic acid) and inorganic acids (e.g. sulfuric acid).

The amount of the base or acid used for the reaction is from a catalytic amount to a large excess per mole of the aniline compound (IX).

As the acylating agent used in the above reaction, there are given an acid anhydride, acid halide, ester and the like, each derived from the carboxylic acid having the formula, R'—COOH, in which R' is as defined above.

The amount of the acylating agent used for the reaction is from 1 mole to a large excess per mole of the aniline compound (IX).

Use of a solvent should be dictated by the kind of the base or acid used, including the case of no solvent used. When a solvent is used, it includes aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate), nitriles (e.g. acetonitrile, isobutyronitrile), amides (e.g. formamide, N,N-dimethylformamide), sulfur compounds (e.g. dimethyl sulfoxide), organic acids (e.g. acetic acid, propionic acid) and the mixtures thereof.

The anilide compound (VIII) can also be prepared starting from the phenol compound of the formula,

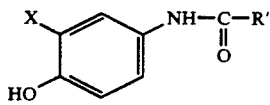

wherein X and R' are as defined above, according to the process disclosed in JP-A-2-138247 (1990), for example.

The aniline compound (IX) is obtained by reducing a nitro compound having the formula (X),

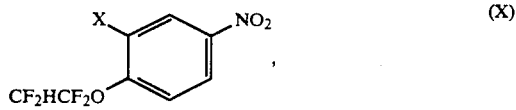

wherein X is as defined above. The reaction can be carried out in the same manner as in the reduction of o-nitroaniline compound (VI).

The nitro compound (X) can be produced starting from a nitrophenol compound having the formula (XI),

wherein X is as defined above, according to the method described in JP-A-2-138247 (1990).

The present compound itself may be used as an active ingredient for agricultural and horticultural fungicides without adding any other ingredients. Usually, however, it is formulated into emulsifiable concentrates, wettable powders, suspension formulations, dusts, granules, dry flowable formulations, etc. by mixing with solid carriers, liquid carriers, gaseous carriers, surface active agents and other auxiliaries for formulation. In this case, the content of the present compound, which is an active ingredient, in the formulations is from 0.01 to 99%, preferably from 0.1 to 80%.

Specific examples of the solid carriers are fine powders or granules of clays (e.g. kaolin clay, diatomaceous earth, synthetic hydrated silicon dioxide, Fubasami clay, bentonite, terra alba), talcs, other inorganic minerals (e.g. sericite, calcite powder, quartz powder, activated carbon, calcium carbonate, hydrated silica), chemical fertilizers (e.g. ammonium sulfate, ammonium phosphate, ammonium nitrate, urea, ammonium chloride), corn stalk powder, walnut shell powder, etc. Specific examples of the liquid carriers are water, alcohols (e.g. methanol, ethanol, ethylene glycol, cellosolve), ketones (e.g. acetone, methyl ethyl ketone, isophorone), aromatic hydrocarbons (e.g. benzene, toluene, xylene, ethylbenzene, methyl naphthalene), aliphatic hydrocarbons (e.g. n-hexane, cyclohexane, kerosene, gas oil), esters (e.g ethyl acetate, butyl acetate), nitriles (e.g. acetonitrile, isobutyronitrile), ethers (e.g. dioxane, diisopropyl ether), acid amides (e.g. dimethylformamide, dimethylacetamide), halogenated hydrocarbons (e.g. dichloroethane, trichloroethylene, carbon tetrachloride), vegetable oils (e.g. soybean oil, cotton seed oil), dimethyl sulfoxide, etc. Specific examples of the gaseous carriers, i.e. a propellant, are freon gas, butane gas, carbon dioxide gas, etc.

Specific examples of the surface active agents are anionic surface active agents such as alkyl sulfates, alkylaryl esters, alkylsulfonates, alkylarylsulfonates, dialkyl sulfosuccinates, the salt of polyoxyethylene alkylaryl ether phosphoric acid esters, naphthalenesulfonic acid/formalin condensates, etc. and nonionic surface active agents such as polyoxyethylene alkyl ether, polyoxyethylene polyoxypropylene block copolymers, sorbitan fatty acid esters, polyhydric alcohol esters, sugar alcohol derivatives, etc.

Specific examples of the fixing agents and dispersing agents are casein, gelatin, polysaccharides [e.g. starch powder, gum arabic, cellulose derivatives {e.g. CMC (carboxymethyl cellulose)}, lignin derivatives {e.g. lignosulfonate}, alginic acid], bentonite, synthetic water-soluble high polymers (e.g. polyvinyl alcohol, polyvinyl pyrrolidone, polyacrylic acids), etc. Specific examples of the stabilizing agents are PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The application method for the present compound are foliar application, soil treatment, seed disinfection and the like. However, any application method which is commonly used by the skilled artisan may be used.

When the present compound is used as an active ingredient for agricultural and horticultural fungicides, the dosage rate of the active ingredient varies with target crops, target diseases, degrees of outbreak of diseases, preparation forms, application methods, application times, weather conditions, etc. Usually, however, the dosage rate is 0.01 to 50 g/are, preferably 0.05 to 10 g/are. When the emulsifiable concentrates, wettable powders, suspension formulations, dry flowable concentrates, etc. are applied diluted with water, the application concentration of the active ingredient is 0.0001 to 0.5%, preferably 0.0005 to 0.2%. The dusts, granules, etc. are applied as they are without being diluted.

As plant diseases which can be controlled with the present compound, for example, the following ones can be given.

Downy mildew of vegetables and Japanese radish (*Peronospora brassicae*), downy mildew of spinach (*Peronospora spinaciae*), downy mildew of tobacco (*Peronospora tabacina*), downy mildew of cucumber (*Pseudoperonospora cubensis*), downy mildew of grape (*Plasmopara viticola*), late blight of apple, strawberry and ginseng (*Phytophthora cactorum*), phytophthora rot of tomato and cucumber (*Phytophthora capsici*), late blight of pineapple (*Phytophthora cinnamomi*), late blight of potato, tomato and eggplant (*Phytophthora infestans*), late blight of tobacco, broad bean and Welsh onion (*Phytophthora nicotianae* var. nicotianae), damping-off of spinach (Pythium sp.), damping-off of cucumber (*Pythium aphanidermatum*), browning root rot of wheat (Pythium sp.), damping-off of tobacco (*Pythium debaryanum*) and pythium rot of soybean (*Pythium aphanidermatum, P. debaryanum, P. irrequlare, P. myriotylum, P. ultimum*).

The present compound can be used as agricultural and horticultural fungicides in plow fields, paddy fields, orchards, tea gardens, pastures, turfs, etc. It can be used in mixture with other agricultural and horticultural fungicides. Further, it can also be used in mixture with insecticides, acaricides, nematocides, herbicides, plant growth regulators and fertilizers.

The present compound has excellent controlling effect on various plant pathogens, particularly plant diseases caused by Phycomycetes such as downy mildew, late blight and the like. Further, the present compound gives no such phytotoxicity as would become a problem to plants to be protected, so that it can be applied to various uses as an active ingredient for agricultural and horticultural fungicides.

The present invention will be illustrated in more detail with reference to the following production examples, formulation examples and test examples, but it is not to be interpreted as being limited to these examples.

First, a production example for the present compound will be shown.

PRODUCTION EXAMPLE 1

3.3 Grams of 2-cyano-5(6)-fluoro-6(5)-(1',1',2',2'-tetrafluoroethoxy)benzimidazole was dissolved in 50 ml of acetonitrile, and after adding 3.5 g of potassium carbonate thereto, the resulting mixture was heated under reflux for 1 hour. Thereafter, 2.94 g of dimethylsulfamoyl chloride was added, and refluxing was continued for 1 hour with heating. The reaction solution was poured into ice water and extracted with ethyl acetate. The organic layer was washed with water, dried over anhydrous magnesium sulfate and concentrated. The residue obtained was subjected to column chromatography on silica gel with chloroform as an eluent to obtain 4.57 g of 2-cyano-1-dimethylsulfamoyl-5(6)-fluoro-6(5)-(1',1',2',2'-tetrafluoroethoxy)benzimidazole [hereinafter referred to as compound (1)].

m.p 105°–112° C. $^1$H-NMR (CDCl$_3$): δ(ppm) 7.60–7.80(2H), 6.05(1H, tt, J=53, 3Hz), 3.15(6H, s)

PRODUCTION EXAMPLE 2

4.2 Grams of 5(6)-chloro-2-cyano-6(5)-(1',1',2',2'-tetrafluoroethoxy)benzimidazole was dissolved in 80 ml of acetonitrile, and after adding 4.7 g of potassium carbonate thereto, the resulting mixture was heated under reflux for 15 minutes. Thereafter, 4.0 g of dimethylsulfamoyl chloride was added, and refluxing was continued for 25 minutes with heating. The reaction solution wa poured into ice water and extracted with ethyl acetate. The organic layer was washed with water, dried over anhydrous magnesium sulfate and concentrated. The residue obtained was subjected to column chromatography on silica gel with chloroform as an eluent and then recrystallized from hexane-ethyl acetate to obtain 2.26 g of 5(6)-chloro-2-cyano-1-dimethylsulfamoyl-6(5)-(1',1',2',2'-tetrafluoroethoxy)benzimidazole [hereinafter referred to as compound (2)]. m.p. 118°–125° C. $^1$H-NMR (CDCl$_3$): δ(ppm) 8.10(about ½H, s), 8.00(about 1H, s), 7.90(about ½H, s), 6.05(1H, tt, J=53, 3 Hz), 3.10(6H, s)

PRODUCTION EXAMPLE 3

3.5 Grams of 5(6)-bromo-2-cyano-6(5)-(1',1',2',2'-tetrafluoroethoxy)benzimidazole was dissolved in 50 ml of acetonitrile, and after adding 3.0 g of potassium carbonate thereto, the resulting mixture was heated under reflux for 30 minutes. Thereafter, 2.0 g of dimethylsulfamoyl chloride was added, and refluxing was continued for 30 minutes with heating. The reaction solution was poured into ice water and extracted with ethyl acetate. The organic layer was washed with water, dried over anhydrous magnesium sulfate and concentrated. The residue obtained was subjected to column chromatography on silica gel with toluene as an eluent and then recrystallized from hexane-ethyl acetate to obtain 3.0 g of 5(6)-bromo-2-cyano-1-dimethylsulfamoyl-6(5)-(1',1',2',2'-tetrafluoroethoxy)benzimidazole [hereinafter referred to as compound (3)].

m.p.: 121.5°–125° C. $^1$H-NMR (CDCl$_3$+DMSO-d$_6$): δ(ppm) 8.15(about ½H, s), 8.05(about ½H, s), 7.85(about ½H), 7.75(about ½H, s), 6.05(1H, tt, J=3, 53 Hz), 3.10(about ½x 6H, s), 3.05(about ½x 6H, s)

Next, production examples for the compound (II) will be shown.

REFERENTIAL EXAMPLE 1

4.67 Grams of 5(6)-fluoro-6(5)-(1',1',2',2'-tetrafluoroethoxy)-2-(trichloromethyl) benzimidazole was dissolved in 25 ml of ethanol. The resulting solution was added by drops to 5.0 ml of a 25% aqueous ammonia at 5° C. After stirring for 2 hours at an inner temperature of 5° C., the reaction solution was poured into a mixture of ice and conc. hydrochloric acid, and extracted with ethyl acetate. The organic layer was washed with water, dried over anhydrous magnesium sulfate and concentrated to obtain 3.3 g of oily 2-cyano-5(6)-fluoro-6(5)-(1',1',2',2'-tetrafluoroethoxy) benzimidazole. $^1$H-NMR (DMSO-d$_6$): δ(ppm) 7.80–7.90(2H), 6.90(1H, tt, J=52, 3 Hz)

REFERENTIAL EXAMPLE 1

5.99 Grams of 5(6)-chloro-6(5)-(1',1',2',2'-tetrafluoroethoxy)-2-(trichloromethyl) benzimidazole was dissolved in 80 ml of ethanol. The resulting solution was added by drops to 30 ml of a 25% aqueous ammonia at 5° C. After stirring for 1 hour and 40 minutes at an inner temperature of 5° C., the reaction solution was poured into a mixture of ice and conc. hydrochloric acid, and extracted with ethyl acetate. The organic layer was washed with water, dried over anhydrous magnesium sulfate, and concentrated to obtain 4.2 g of oily 5(6)-chloro-2-cyano-6(5)(1',1',2',2'-tetrafluoroethoxy)benzimidazole. ethoxy)benzimidazole. $^1$H-NMR (CDCl$_3$): δ(ppm) 8.00(1H, s), 7 80(1H, s), 6.80(1H, tt, J=52, 3 Hz)

REFERENTIAL EXAMPLE 3

5.0 Grams of 5(6)-bromo-6(5)-(1',1',2',2'-tetrafluoroethoxy)-2-(trichloromethyl) benzimidazole was dissolved in 50 ml of ethanol. The resulting solution was added by drops to 30 ml of a 25% aqueous ammonia at 5°–10° C. After stirring for 50 minutes at an inner temperature of 5° C., the reaction solution was poured into a mixture of ice and conc. hydrochloric acid, and extracted with ethyl acetate. The organic layer was washed with water, dried over anhydrous magnesium sulfate, and concentrated to obtain 3.5 g of 5(6)-bromo-2-cyano-6(5)-(1',1',2',2'-tetrafluoroethoxy)-benzimidazole. $^1$H-NMR (CDCl$_3$+DMSO-d$_6$): δ(ppm) 7.85(1H, s), 7.55(1H), 6.05(1H, tt, J=3, 52 Hz)

Next, production examples for the compound (III) will be shown.

REFERENTIAL EXAMPLE 4

3.9 Grams of 4-fluoro-5-(1',1',2',2'-tetrafluoroethoxy)-1,2-benzenediamine, [i.e. the o-phenylenediamine compound (IV) containing fluorine as the substituent X] was dissolved in 50 ml of acetic acid, 3.5 g of methyl trichloroacetoimidate was added thereto at room temperature, and the resulting mixture was stirred for 15 minutes. The reaction solution was poured into ice water and extracted with ethyl acetate. The organic layer was washed with water, dried over anhydrous magnesium sulfate and concentrated to obtain 4.9 g of 5(6)-fluoro-6(5)-(1',1',2',2'-tetrafluoroethoxy)-2-(trichloromethyl) benzimidazole. $^1$H-NMR (DMSO-d$_6$): δ(ppm) 7.70–7.90(2H), 6.95(1H, tt, J=52, 3 Hz)

REFERENTIAL EXAMPLE 5

5.2 Grams of 4-chloro-5-(1',1',2',2'-tetrafluoroethoxy)-1,2-benzenediamine, [i.e. the o-phenylenediamine compound (IV) containing chlorine as the substituent X] was dissolved in 70 ml of acetic acid, 4.0 g of trichloroacetoimidate was added thereto at room temperature, and the resulting mixture was stirred for 15 minutes. The reaction solution was poured into ice water and extracted with ethyl acetate. The organic layer was washed with a saturated aqueous solution of sodium hydrogencarbonate, washed with water, dried over anhydrous magnesium sulfate, and concentrated to obtain 5.99 g of 5(6)-chloro-6(5)-(1',1',2',2'-tetrafluoroethoxy)-2-(trichloromethyl) benzimidazole. $^1$H-NMR (CDCl$_3$): δ(ppm) 8.00(1H, s), 7.85(1H, s), 6.95(1H, tt, J=52, 3 Hz)

REFERENTIAL EXAMPLE 6

9.5 Grams of 4-bromo-5-(1',1',2',2'-tetrafluoroethoxy)-1,2-benzenediamine, [i.e. the o-phenylenediamine compound (IV) containing bromine as the substituent X] was dissolved in 100 ml of acetic acid, 5.7 ml of methyl trichloroacetoimidate was added thereto at room temperature, and the resulting mixture was stirred for 20 minutes. The reaction solution was poured into ice water and extracted with ethyl acetate. The organic layer was washed with water, dried over anhydrous magnesium sulfate, and recrystallized from hexane-ethyl acetate to obtain 5.0 g of 5(6)-bromo-6(5)-(1',1',2',2'-tetrafluoroethoxy)-2-tetrafluoroethoxy)-2-(trichloromethyl)-benzimidazole. $^1$H-NMR (CDC$_{33}$+DMSO-d$_6$): δ(ppm) (1H, s), 7.45(1H), 5.97(1H, tt, 7.77 (1H, s), 7.45(1H), 5.97 (1H, tt, J=3, 53 Hz)

Next, production examples for the o-phenylenediamine compound (IV) will be shown.

REFERENTIAL EXAMPLE 7

4.7 Grams of 5-fluoro-2-nitro-4-(1',1',2',2'-tetrafluoroethoxy)aniline [i.e. the o-nitroaniline compound (VI) containing fluorine as the substituent X] was dissolved in a mixed solvent of 15 ml of ethyl acetate and 15 ml of acetic acid. The resulting solution was dropwise added to a suspension of 4.8 g of iron powders in a mixed solution of 3 ml of acetic acid and 30 ml of water while maintaining the temperature at 40° C. Thereafter, stirring was continued for 15 minutes at 40° C. to 50° C. The reaction solution was filtered through Celite, and the filtrate was extracted with ethyl acetate. The organic layer was washed with an aqueous sodium hydrogencarbonate solution and water in this order, dried over anhydrous magnesium sulfate and concentrated. The residue obtained was subjected to column chromatography on silica gel with chloroform as an eluent to obtain 3.9 g of 4-fluoro-5-(1',1',2',2'-tetrafluoroethoxy)-1,2-benzenediamine [i.e. the o-phenylenediamine compound (IV) containing fluorine as the substituent X]. $^1$H-NMR (CDCl$_3$): δppm 6.40–6.70(2H), 5.90(1H, tt, J=54, 3 Hz), 3.30(4H, broad).

REFERENTIAL EXAMPLE 8

5.6 Grams of 5-chloro-2-nitro-4-(1',1',2',2'-tetrafluoroethoxy)aniline [i.e. the o-nitroaniline compound (VI) containing chlorine as the substituent X] was dissolved in a mixed solvent of 25 ml of ethyl acetate and 25 ml of acetic acid. The resulting solution was dropwise added to a suspension of 4.7 g of iron powders in a mixed solution of 5 ml of acetic acid and 50 ml of water while maintaining the temperature at 50° C. Thereafter, stirring was continued for 20 minutes at 50° C. to 60° C. The reaction solution was filtered through Celite, and the filtrate was extracted with ethyl acetate. The organic layer was washed with an aqueous sodium hydrogencarbonate solution and water in this order, dried over anhydrous magnesium sulfate and concentrated. The residue obtained was subjected to column chromatography on silica gel with chloroform and ethyl acetate as eluents to obtain 5.2 g of 4-chloro-5-(1',1',2',2'-tetrafluoroethoxy)-1,2-benzenediamine [i.e. the o-phenylenediamine compound (IV) containing chlorine as the substituent X]. $^1$H-NMR (CDCl$_3$): δ(ppm) 6.65–6.75(2H), 5.95(1H, tt, J=53, 3 Hz), 3.40(4H, s, broad)

REFERENCE EXAMPLE 9

10.5 Grams of 5-bromo-2-nitro-4-(1',1',2',2'-tetrafluoroethoxy)aniline [i.e. the o-nitroaniline compound (VI) containing bromine as the substituent X] was dissolved in a mixed solvent of 25 ml of ethyl acetate and 25 ml of acetic acid. The resulting solution was dropwise added to a suspension of 5.0 g of iron powders in a mixed solution of 7 ml of acetic acid and 50 ml of water while maintaining the temperature at 45°–70° C. Thereafter, stirring was continued for 10 minutes within the same temperature range. The reaction solution was filtered through Celite, and the filtrate was extracted with ethyl acetate. The organic layer was washed with an aqueous sodium hydrogencarbonate solution and water in this order, dried over anhydrous magnesium sulfate and concentrated to obtain 9.5 g of 4-bromo-5-(1',1',2',2'-tetrafluoroethoxy) -1,2-benzenediamine. $^1$H-NMR (CDCl$_3$): δ(ppm) 6.78(1H, s), 6.60(1H), 5.90(1H, tt, J=3, 52 Hz), 3.45(4H, broad)

Next, production examples for the o-nitroaniline compound (VI) will be shown.

REFERENTIAL EXAMPLE 10

A mixture of 5.96 g of 5-fluoro-2-nitro-4-(1',1',2',2'-tetrafluoroethoxy)acetoanilide, 25 ml of conc. hydrochloric acid and 250 ml of methanol was heated under reflux for 2 hours. The reaction solution was concentrated poured into ice water and alkalified with potassium carbonate. After extracting the resulting solution with ethyl acetate, the organic layer was washed with water and dried over anhydrous magnesium sulfate. The solvent was removed by distillation to obtain 4.7 g of 5-fluoro-2-nitro-4-(1',1',2',2'-tetrafluoroethoxy)aniline [i.e. the o-nitroaniline compound (VI) containing fluorine as the substituent X]. $^1$H-NMR (CDCl$_3$): δ(ppm) 8.15(1H, d, J=7 Hz), 6.70(1H, d, J=11 Hz), 6.30(2H, broad), 6.00(1H, tt, J=52, 3 Hz)

REFERENTIAL EXAMPLE 11

A mixture of 6.84 g of 5-chloro-2-nitro-4-(1',1',2',2'-tetrafluoroethoxy)acetoanilide, 20 ml of conc. hydrochloric acid and 100 ml of methanol was heated under reflux for 3 hours. The reaction solution was concentrated, poured into ice water and alkalified with potassium carbonate. After extracting the resulting solution with ethyl acetate, the organic layer was washed with water and dried over anhydrous magnesium sulfate. The solvent was removed by distillation to obtain 5.6 g of 5-chloro-2-nitro-4-(1',1',2',2'-tetrafluoroethoxy)aniline [i.e. the o-nitroaniline compound (VI) containing chloro as the substituent X]. $^1$H-NMR (CDCl$_3$): δ(ppm) 8.10(1H, s), 6.98(1H, s), 6.25(2H, broad), 5.98(1H, tt, 53, 3 Hz)

REFERENTIAL EXAMPLE 12

A mixture of 11.9 g of 5-bromo-2-nitro-4-(1',1',2',2'-tetrafluoroethoxy)acetoanilide, 10 ml of conc. hydrochloric acid and 100 ml of methanol was heated under reflux for 40 minutes. The reaction solution was concentrated, poured into ice water and alkalified with potassium carbonate. After extracting the resulting solution with ethyl acetate, the organic layer was washed with water and dried over anhydrous magnesium sulfate. The solvent was removed by distillation to obtain 10.5 g of 5-bromo-2-nitro-4-(1',1',2',2'-tetrafluoroethoxy)aniline [i.e. the o-nitroaniline compound (VI) containing bromine as the substituent X]. $^1$H-NMR (CDCl$_3$): δ(ppm) 7.80(1H, s), 6.90(1H, s), 6.10(2H, broad), 5.80(1H, tt, J=3, 55 Hz)

Next, production examples for the 2-nitroanilide compound (VII) will be shown.

REFERENTIAL EXAMPLE 13

4.75 Grams of 3-fluoro-4-(1',1',2',2'-tetrafluoroethoxy)acetoanilide was added to 50 ml of conc. sulfuric acid, and to the resulting mixture was dropwise added a mixture of 4 ml of fuming nitric acid and 8 ml of conc. sulfuric acid while maintaining the temperature at −30° C. After addition, the reaction solution was stirred for 1 hour at −30° C. to −20° C. The reaction solution was poured into ice water, and the precipitated crystals were filtered off. The crystals were dissolved in ethyl acetate, and the resulting solution was washed with water and dried over anhydrous magnesium sulfate. The residue obtained by removing the solvent by distillation was subjected to column chromatography on silica gel with chloroform as an eluent to obtain 5.0 g of 5-fluoro-2-nitro-4-(1',1',2',2'-tetrafluoroethoxy)acetoanilide [i.e. the 2-nitroanilide compound (VII) in which X is fluorine and R' is methyl]. $^1$H-NMR (CDCl$_3$): δ(ppm) 10.35(1H, broad), 8.85(1H, d, J=12 Hz), 8.25(1H, d, J=7 Hz), 6.05(1H, tt, J=53, 3 Hz), 2.35(3H, s)

REFERENTIAL EXAMPLE 14

7.7 Grams of 3-chloro-4-(1',1',2',2'-tetrafluoroethoxy)acetoanilide was added to 70 ml of conc. sulfuric acid, and to the resulting mixture was dropwise added a mixture of 7 ml of fuming nitric acid and 15 ml of conc. sulfuric acid while maintaining the temperature at −20° C. After addition, the reaction solution was stirred for 1 hour and 20 minutes at −20° C. to −15° C. The reaction solution was poured into ice water, and the precipitated crystals were filtered off. The crystals were dissolved in ethyl acetate, and the resulting solution was washed with water and dried over anhydrous magnesium sulfate. The residue obtained by removing the solvent by distillation was subjected to column chromatography on silica gel with chloroform as an eluent to obtain 6.84 g of 5-chloro-2-nitro-4-(1',1',2',2'-tetrafluoroethoxy)acetoanilide [i.e. the 2-nitroanilide compound (VII) in which X is chlorine and R' is methyl]. $^1$H-NMR (CDCl$_3$): δ(ppm) 9.05(1H, s), 8.20(1H, s), 6.00(1H, tt, J=52, 3 Hz), 2.30(3H, s)

REFERENTIAL EXAMPLE 15

11.3 Grams of 3-bromo-4-(1',1',2',2'-tetrafluoroethoxy)acetoanilide was added to 100 ml of conc. sulfuric acid, and to the resulting mixture was dropwise added a mixture of 7 ml of fuming nitric acid and 15 ml of conc. sulfuric acid while maintaining the temperature at −20° C. After addition, the reaction solution was stirred for 1 hour at −20° C. The reaction solution was poured into ice water, and the precipitated crystals were filtered off. The crystals were dissolved in ethyl acetate, and the resulting solution was washed with water and dried over anhydrous magnesium sulfate. Removing the solvent by distillation from the residue gave 11.9 g of 5-bromo-2-nitro-4-(1',1',2',2'-tetrafluoroethoxy)acetoanilide [i.e. the 2-nitroanilide compound (VII) in which X is bromine and R' is methyl]. $^1$H-NMR (CDCl$_3$+DMSO-d$_6$): δ(ppm) 10.20(1H, broad), 8.65(1H, s), 8.00(1H, s), 6.40(1H, tt, J=3, 52 Hz)

Next, production examples for the anilide compound (VIII) will be shown.

REFERENTIAL EXAMPLE 16

5.35 Grams of 3-fluoro-4-(1',1',2',2'-tetrafluoroethoxy)aniline [i.e. the aniline compound (IX) containing fluorine as the substituent X] was dissolved in a mixture of 50 ml of acetic acid and 6 ml of acetic anhydride, and the resulting solution was stirred at 90° C. for 15 minutes. The reaction solution was poured into ice water, and the precipitated crystals were filtered off. The crystals were dissolved in ethyl acetate, and the resulting solution was washed with water and dried over anhydrous magnesium sulfate. The solvent was then removed by distillation to obtain 5.66 g of 3-fluoro-4-(1',1',2',2'-tetrafluoroethoxy)acetoanilide [i.e. the anilide compound (VIII) in which X is fluorine and R' is methyl]. $^1$H-NMR (CDCl$_3$): δ(ppm) 8.10(1H, broad), 7.60(1H, dd, J=11, 2 Hz), 7.05–7.25(2H, m), 5.90(1H, tt, J=53, 3 Hz), 2.05(3H, s)

REFERENTIAL EXAMPLE 17

8.09 Grams of 3-chloro-4-(1',1',2',2'-tetrafluoroethoxy)aniline [i.e. the aniline compound (IX) containing chlorine as the substituent X] was dissolved in a mixture of 100 ml of acetic acid and 3.5 ml of acetic anhydride, and the resulting solution was stirred at 90° C. for 25 minutes. The reaction solution was poured into ice water, and the precipitated crystals were filtered off. The crystals were dissolved in ethyl acetate, and the resulting solution was washed with water and dried over anhydrous magnesium sulfate. The solvent was then removed by distillation to obtain 7.73 g of 3-chloro-4-(1',1',2',2'-tetrafluoroethoxy)acetoanilide [i.e. the anilide compound (VIII) in which X is chlorine and R' is methyl]. $^1$H-NMR (CDCl$_3$): δ(ppm) 8.90(1H, broad), 7.88(1H, d, J=2 Hz), 7.30(1H, d, J=2 Hz), 7.28(1H, s), 5.95(1H, tt, J=53, 3 Hz), 2.20(3H, s)

REFERENTIAL EXAMPLE 18

10.6 Grams of 2-bromo-4-acetamidephenol was dissolved in 100 ml of N,N-dimethlformamide. 2.0 Grams of potassium hydroxide was added thereto. Tetrafluoroethylene was blown into the solution at room temperature. The tetrafluoroethylene-blown solution was stirred for 1 hour and 30 minutes at an inner temperature of 70° C. The reaction solution was poured into ice water. The resulting mixture was extracted with ether. The organic layer was washed with water, dried over anhydrous magnesium sulfate and concentrated. The residue obtained was subjected to column chromatography on silica gel with chloroform and ethyl acetate as eluents to obtain 11.3 g of 3-bromo-4-(1',1',2',2'-tetrafluoroethoxy)acetoanilide. $^1$H-NMR (CDCl$_3$): δ(ppm) 9.00(1H, broad), 7.85(1H, d, J=2 Hz), 7.35(1H, dd, J=2, 9 Hz), 7.10(1H, d, J=9 Hz), 5.85(1H, tt, J=3, 53 Hz), 2.05 (3H, s)

Next, production examples for the aniline compound (IX will be shown.

REFERENTIAL EXAMPLE 19

6.97 Grams of 3-fluoro-4-(1',1',2',2'-tetrafluoroethoxy)nitrobenzene [i.e. the nitro compound (X) containing fluorine as the substituted X] was dissolved in a mixed solvent of 25 ml of ethyl acetate and 25 ml of acetic acid. The resulting solution was slowly added dropwise to a suspension of 9.0 g of iron powders in a mixed solution of 5 ml of acetic acid and 30 ml of water while maintaining the temperature at 40° C. Thereafter, stirring was continued for 30 minutes at 40° C. to 70° C. The reaction solution was filtered through Celite, and the filtrate was extracted with ethyl acetate. The organic layer was washed with an aqueous sodium hydrogencarbonate solution and then with water, dried over anhydrous magnesium sulfate and concentrated. The residue obtained was subjected to column chromatography on silica gel with chloroform as an eluent to obtain 5.35 g of 3-fluoro-4-(1',1',2',2'-tetrafluoroethoxy)aniline [i.e. the aniline compound (IX) containing fluorine as the substituted X]. $^1$H-NMR (CDCl$_3$): δ(ppm) 6.90-7.30(1H, m), 6.30-6.60(2H), 5.95(1H, tt, J=53, 3 Hz), 3.75(2H, broad)

REFERENTIAL EXAMPLE 20

12.5 Grams of 3-chloro-4-(1',1',2',2'-tetrafluoroethoxy)nitrobenzene [i.e. the nitro compound (X) containing chlorine as the substituted X] was dissolved in a mixed solvent of 50 ml of ethyl acetate and 50 ml of acetic acid. The resulting solution was slowly added dropwise to a suspension of 12.2 g of iron powders in a mixed solution of 13 ml of acetic acid and 130 ml of water while maintaining the temperature at 40° C. Thereafter, stirring was continued for 30 minutes at 40° C. to 60° C. The reaction solution was filtered through Celite, and the filtrate was extracted with ethyl acetate. The organic layer was washed with an aqueous sodium hydrogencarbonate solution and then with water, dried over anhydrous magnesium sulfate and concentrated. The residue obtained was subjected to column chromatography on silica gel with chloroform as an eluent to obtain 9.41 g of 3-chloro-4-(1',1',2',2'-tetrafluoroethoxy)aniline [i.e. the aniline compound (IX) containing chlorine as the substituted X]. $^1$H-NMR (CDCl$_3$): δ(ppm) 7.10(1H, d, J=9 Hz , 6.70(1H, d, J=3 Hz), 6.48(1H, dd, J=9, 3 Hz), 5.95(1H, tt, J=53, 3 Hz), 3.65(2H, broad)

Next, production examples for the nitro compound (X will be shown.

REFERENTIAL EXAMPLE 21

7.0 Grams of 2-fluoro-4-nitrophenol was dissolved in 70 ml of N,N-dimethylformamide, and 1.0 g of potassium hydroxide was added thereto. Tetrafluoroethylene was blown into the resulting solution at an inner temperature of 100° C., after which stirring was continued for 6 hours at an inner temperature of 100° C. The reaction solution was poured into ice water and extracted with ether. The organic layer was washed with water, dried over anhydrous sodium sulfate and concentrated. The residue obtained was subjected to column chromatography on silica gel with toluene as an eluent to obtain 6.97 g of 3-fluoro-4-(1',1',2',2'-tetrafluoroethoxy)nitrobenzene. $^1$H-NMR (CDCl$_3$): δ(ppm) 7.10-8.2(3H), 5.59(1H, tt, J=53, 3 Hz)

REFERENTIAL EXAMPLE 22

20 Grams of 2-chloro-4-nitrophenol was dissolved in 200 ml of N,N-dimethylformamide, and 3.4 g of potassium hydroxide was added thereto. Tetrafluoroethylene was blown into the resulting solution at an inner temperature of 50° C., after which stirring was continued for 50 minutes at an inner temperature of 50° C. Thereafter, 3.5 g of potassium hydroxide was added to the stirred solution and the resulting solution was further stirred for 6 hours at an inner temperature of 100° C. The reaction solution was poured into ice water and extracted with ether. The organic layer was washed with water, dried over anhydrous sodium sulfate and concentrated. The residue obtained wa subjected to column chromatography on silica gel with chloroform as an eluent to obtain 12.55 g of 3-chloro-4-(1',1',2',2'-tetrafluoroethoxy)nitrobenzene. $^1$H-NMR (CDCl$_3$): δ(ppm) 8.37(1H, d, J=3 Hz), 8.20(1H, dd, J=9, 3 Hz), 7.57(1H, d, J=9 Hz), 6.07(1H, tt, J=53, 3 Hz)

Next, formulation examples will be shown. In the examples, all parts are by weight.

FORMULATION EXAMPLE 1

50 Parts of each of the present compounds (1), (2) and (3), 3 parts of calcium lignosulfonate, 2 parts of sodium lauryl sulfate and 45 parts of synthetic hydrated silicon dioxide are well pulverized and mixed to obtain a wettable powder of each of the present compounds (1), (2) and (3).

FORMULATION EXAMPLE 2

25 Parts of each of the present compounds (1), (2) and (3), 3 parts of polyoxyethylene sorbitan monooleate, 3 parts of CMC and 69 parts of water are mixed. The resulting mixture is wet-pulverized until the particle size of the active ingredient is reduced to 5 microns or less to obtain a suspension formulation of each of the present compounds (1), (2) and (3).

FORMULATION EXAMPLE 3

2 Parts of each of the present compounds (1), (2) and (3), 88 parts of kaolin clay and 10 parts of talc are well pulverized and mixed to obtain a dust of each of the present compounds (1), (2) and (3).

FORMULATION EXAMPLE 4

20 Parts of each of the present compounds (1), (2) and (3), 14 parts of polyoxyethylene styrylphenyl ether, 6 parts of calcium dodecylbenzenesulfonate and 60 parts of xylene are well mixed to obtain an emulsifiable concentrate of each of the present compounds (1), (2) and (3).

FORMULATION EXAMPLE 5

2 Parts of each of the present compounds (1), (2) and (3), 1 part of synthetic hydrated silicon dioxide, 2 parts of calcium lignosulfonate, 30 parts of bentonite and 65 parts of kaolin clay are well pulverized and mixed. The resulting mixture is well kneaded with water, granulated and dried to obtain a granule of each of the present compounds (1), (2) and (3).

Next, the usefulness of the present compound as an agricultural and horticultural fungicide will be shown by test examples. As a control, a compound of the following formula [hereinafter referred to as (A)] described in JP-A-62-205063 was used.

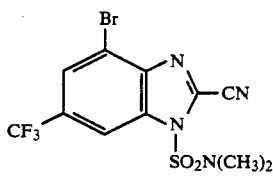

The controlling activity was evaluated in six stages, 5, 4, 3, 2, 1, 0, of the controlling index by macroscopically observing the condition of disease of the test plants, i.e. the degrees of colony and infected area on the leaves, stems, etc., at the time of examination.

5 Infected area is not observed at all.
4 Size of infected area is less than 10% of that in the untreated plot.
3 Size of infected area is less than 30% of that in the untreated plot.
2 Size of infected area is less than 50% of that in the untreated plot.
1 Size of infected area is less than 75% of that in the untreated plot.
0 Size of infected area is 75% or more of that in the untreated plot.

Test Example 1 Controlling test on late blight of tomato (*Phytophthora infestans*) (preventive effect)

Sandy loam was filled in plastic pots, and tomato (var., Ponterosa) was sowed and cultivated for 20 days in a greenhouse to obtain tomato seedlings in the 2nd to 3rd true leaf stage. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were inoculated by spraying the spore suspension of *Phytophthora infestans*. After the inoculation, the seedlings were kept in conditions of 20° C. and high humidity for 1 day and further cultivated for 7 days under lighting. The controlling activity was then examined. The results are shown in Table 1.

TABLE 1

| Test compound | | |
|---|---|---|
| Compound | Application concentration of active ingredient (ppm) | Controlling activity |
| (1) | 12.5 | 5 |
|  | 3.1 | 5 |
| (2) | 12.5 | 5 |
|  | 3.1 | 5 |

Test Example 2 Controlling test on late blight of tomato (*Phytophthora infestans*) (curative effect)

Sandy loam was filled in plastic pots, and tomato (var., Ponterosa) was sowed and cultivated for 20 days in a greenhouse to obtain tomato seedlings in the 2nd to 3rd true leaf stage. The seedlings were inoculated by spraying the spore suspension of *phytophthora infestans*. After the inoculation, the seedlings were kept in conditions of 20° C. and high humidity for 1 day. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were cultivated for 7 days under lighting. The controlling activity was then examined. The results are shown in Table 2.

TABLE 2

| Test compound | | |
|---|---|---|
| Compound | Application concentration of active ingredient (ppm) | Controlling activity |
| (1) | 200 | 5 |
|  | 50 | 3 |
| (2) | 200 | 5 |
|  | 50 | 3 |

Test Example 3 Controlling test on downy mildew of grape (*Plasmopara viticola*) (preventive effect)

Sandy loam was filled in plastic pots, and grape was sowed and cultivated for 50 days in a greenhouse to obtain grape seedlings in the 3rd to 4th true leaf stage. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were inoculated by spraying the spore suspension of *Plasmopara viticola*. After the inoculation, the seedlings were kept in conditions of 20° C. and high humidity for 1 day and further cultivated for 7 days under lighting. The controlling activity was then examined. The results are shown in Table 3.

TABLE 3

| Test compound | | |
|---|---|---|
| Compound | Application concentration of active ingredient (ppm) | Controlling activity |
| (1) | 12.5 | 5 |
|  | 3.1 | 5 |
| (2) | 12.5 | 5 |
|  | 3.1 | 5 |

Test Example 4 Controlling test on downy mildew of grape (*Plasmopara viticola*) (curative effect)

Sandy loam was filled in plastic pots, and grape was sowed and cultivated for 50 days in a greenhouse to obtain grape seedlings in the 3rd to 4th true leaf stage. The seedlings were inoculated by spraying the spore suspension of *Plasmopara viticola*. After the inoculation, the seedlings were kept in conditions of 20° C. and high humidity for 1 day. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were cultivated for 7 days under lighting. The controlling activity was then examined. The results are shown in Table 4.

TABLE 4

| Test compound | | |
|---|---|---|
| Compound | Application concentration of active ingredient (ppm) | Controlling activity |
| (1) | 50 | 5 |
| | 12.5 | 3 |
| (2) | 50 | 5 |
| | 12.5 | 3 |
| (A) | 50 | 2 |
| | 12.5 | 1 |

Test Example 5 Controlling test on downy mildew of cucumber (*Pseudoperonospora cubensis*) (preventive effect)

Sandy loam was filled in plastic pots, and cucumber (var., Sagamihanjiro) was sowed and cultivated for 14 days in a greenhouse to obtain cucumber seedlings. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were inoculated by spraying the spore suspension of *Pseudoperonospora cubensis*. After the inoculation, the seedlings were kept in conditions of 20° C. and high humidity for 1 day and further cultivated for 7 days under lighting. The controlling activity was then examined. The results are shown in Table 5.

TABLE 5

| Test compound | | |
|---|---|---|
| Compound | Application concentration of active ingredient (ppm) | Controlling activity |
| (1) | 12.5 | 5 |
| | 3.1 | 5 |
| (2) | 12.5 | 5 |
| | 3.1 | 5 |

Test Example 6 Controlling test on downy mildew of cucumber (*Pseudoperonospora cubensis*) (curative effect)

Sandy loam was filled in plastic pots, and cucumber (var., Sagamihanjiro) was sowed and cultivated for 14 days in a greenhouse to obtain cucumber seedlings. The seedlings were inoculated by spraying the spore suspension of *Pseudoperonospora cubensis*. After the inoculation, the seedlings were kept in conditions of 20° C. and high humidity for 1 day. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were cultivated for 7 days under lighting. The controlling activity was then examined. The results are shown in Table 6.

TABLE 6

| Test compound | | |
|---|---|---|
| Compound | Application concentration of active ingredient (ppm) | Controlling activity |
| (1) | 50 | 5 |
| | 12.5 | 5 |
| | 3.1 | 5 |
| (2) | 50 | 5 |
| | 12.5 | 5 |
| | 3.1 | 5 |
| (A) | 50 | 3 |
| | 12.5 | 2 |
| | 3.1 | 2 |

Test Example 7 Controlling test on late blight of potato (*Phytophthora infestans*) (preventive effect)

Sandy loam was filled in plastic pots, and potato (var., Danshaku) was sowed and cultivated for 20 days in a greenhouse to obtain potato seedlings. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were inoculated by spraying the spore suspension of *Phytophthora infestans*. After the inoculation, the seedlings were kept in conditions of 20° C. and high humidity for 1 day and further cultivated for 8 days under lighting. The controlling activity was then examined. The results are shown in Table 7.

TABLE 7

| Test compound | | |
|---|---|---|
| Compound | Application concentration of active ingredient (ppm) | Controlling activity |
| (1) | 50 | 5 |
| | 12.5 | 5 |
| | 3.1 | 4 |

Test Example 8 Phytotoxicity test

The wettable powder of the test compound prepared according to Formulation Example 1 was diluted with water to a prescribed concentration and foliar-applied onto the seedlings of cucumber (var., Sagami hanjiro) so that the spray liquor thoroughly adhered to the leaf surface. After the spraying, the seedlings were cultivated for 2 weeks in a greenhouse, and the condition of leaves of the test plant was macroscopically observed to examine the degree of phytotoxicity. As a result, both the compounds (1) and (2) showed no phytotoxicity at all at the application concentrations of 1,000 ppm and 500 ppm.

What is claimed is:

1. A compound of the formula,

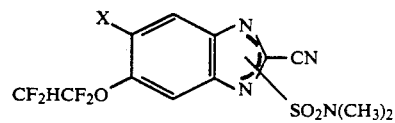

wherein X is halogen.

2. A compound according to claim 1, wherein X is fluorine.

3. A compound according to claim 1, wherein X is chlorine.

4. A compound according to claim 1, wherein X is bromine.

5. An agricultural and horticultural fungicidal composition which comprises as an active ingredient a fungicidally effective amount of a compound according to claim 1.

6. A method for controlling plant diseases which comprises applying a fungicidally effective amount of a compound according to claim 1 to plants.

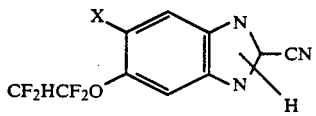

wherein X is halogen, with dimethylsulfamoyl chloride optionally in the presence of a base.

7. A compound of the formula,

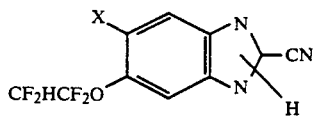

wherein X is halogen.

8. A compound according to claim 7, wherein X is fluorine.

9. A compound according to claim 7, wherein X is chlorine.

10. A compound according to claim 7, wherein X is bromine.

11. A compound of the formula,

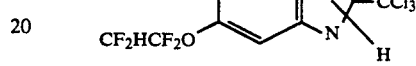

wherein X is halogen.

12. A compound according to claim 11, wherein X is fluorine.

13. A compound according to claim 11, wherein X is chlorine.

14. A compound according to claim 11, wherein X is bromine.

* * * * *